Jan. 22, 1974 B. J. MACHIN Plant Pat. 3,450
CHRYSANTHEMUM PLANT
Filed Dec. 27, 1971
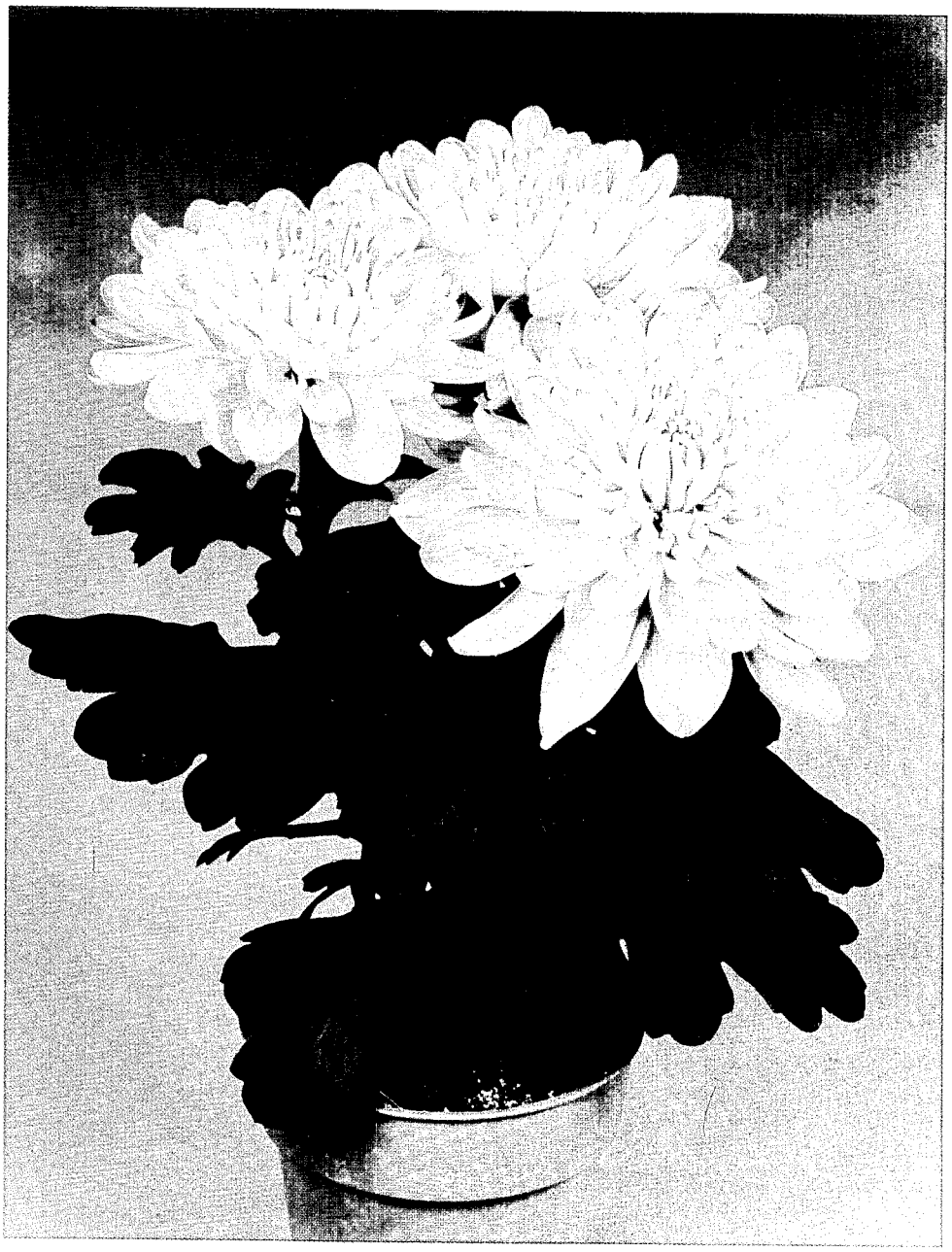

United States Patent Office

Plant Pat. 3,450
Patented Jan. 22, 1974

3,450
CHRYSANTHEMUM PLANT

Barrie John Machin, East Broyle Estate, Chichester, England, assignor to Frampton's Nurseries Limited, Chichester, Sussex, England Filed Dec. 27, 1971, Ser. No. 212,838
Int. Cl. A01h 5/00
U.S. Cl. Plt.—80 1 Claim This invention relates to a new and distinct variety of *Chrysanthemum morifolium* Bailey (pot type) known as Louise. Louise is a seedling originated by me from a cross made in 1966 between the unpatented variety Bluebell and the unpatented variety Apricot Princess Anne, the former being the seed parent and the latter being the pollen parent.

The variety Louise resulted from an extensive breeding program with the object of producing improved varieties for year round pot chrysanthemum production with more uniformity and reduced flowering time compared with existing varieties. Louise has the following improved characteristics over Princess Anne varieties, including its pollen parent:

(1) It is much more responsive and will produce good quality pot plants in 2–3 weeks less growing time round the year.
(2) It is much easier to control the height of the plant and little or no chemical dwarfing measures are required.
(3) Although flowers are smaller, their form is improved and more flowers per plant are obtained.
(4) As compared with Apricot Princess Anne, Louise has flowers which are pink rather than yellow.
(5) Quality of petal is improved in poor winter light conditions.

As compared with its seed parent, Louise has a flower of firmer texture and a more formal incurving shape, a deeper color and, a more uniform and slightly earlier response in winter conditions. The plant is more widely branched and stocky.

As compared with its seed parent, Louise is much more responsive under a wide range of environmental conditions and will produce a flowering pot plant in 2–3 weeks less growing time. It produces more breaks after the pinch and is more easily controlled regarding plant height. Petal quality is improved under poor winter light conditions.

Asexual reproduction of this new variety Louise by rooting vegetative shoots in Sussex, England, shows that the above characteristics are fixed and come true to type through succeeding generations.

The accompanying drawing shows a typical flower of my new variety depicted in color as nearly true as it is reasonably possible to make the same in a color illustration of this character.

The following is a detailed description of the new variety Louise with color terminology in accordance with the Royal Horticultural Society color chart, hereinafter referred to as RHS.

Genus: Chrysanthemum
Species: *Morifolium* Bailey
Type: Pot
Class: Incurving decorative
Breeding: The original seedling resulted from a cross between the varieties Bluebell and Apricot Princess Anne, the former being the seed parent, and the latter being the pollen parent. The cross was made in 1966 at Frampton's Nurseries Ltd., Chichester, Sussex, England.
Propagation: Holds its distinguishing characteristics through succeeding propagations by rooting vegetative shoots.
Flower: When grown and observed in Sussex, England, in 3½ inch pots and pinched, up to 6 flowers per plant are formed. When five plants are planted per 5 inch pot, 4 to 5 flowers are borne on each plant.
Bloom:
*Size.*—Average diameter is 8 cm. when fully open.
*Petalage.*—Decorative, with approximately 150 to 200 ray petals and 10 to 20 disc petals.
*Form.*—Incurving decorative.
*Petals.*—Medium length, broad, overlapping, blunt, flat and of thick texture.
Color of open bloom:
Inner face of fully expanded petal, RHS 70D.
Outer face of fully expanded petal, RHS 65D.
Inner face of young petal, RHS 70D.
Outer face of young petal, RHS 65D.

The tips of the outer faces of the young ray petals are initially RHS 20B, but this color fades completely as the petals expand and is invisible in mature petals.
Response group: 8 weeks.
Temperature tolerance: 55–60° F. at night.
Plant: Stocky, well branched habit of growth.
Foliage:
Medium quality.
Average internode length, 1½ to 2 cm.
Medium size.
Color, RHS 144A.
Medium texture.
Stem:
Thick and strong.
Color, RHS 144C at flowering.

I claim:

1. A new and distinct variety of *Chrysanthemum morifolium* Bailey (pot type), substantially as herein shown and described, characterized particularly as to novelty by the unique combination of a reduced response period, an increased number of flowers per plant, and improved quality of petal in poor winter light conditions.

No references cited.

ROBERT E. BAGWILL, Primary Examiner